United States Patent [19]
Zhu et al.

[11] Patent Number: 5,597,467
[45] Date of Patent: Jan. 28, 1997

[54] SYSTEM FOR INTERFACING CAPILLARY ZONE ELECTROPHORESIS AND INDUCTIVELY COUPLED PLASMA-MASS SPECTROMETER SAMPLE ANALYSIS SYSTEMS, AND METHOD OF USE

[75] Inventors: Jianzhong Zhu; Daniel R. Wiederin, both of Omaha, Nebr.

[73] Assignee: Cetac Technologies Inc., Omaha, Nebr.

[21] Appl. No.: 391,152

[22] Filed: Feb. 21, 1995

[51] Int. Cl.⁶ .................... G01N 27/26; G01N 27/447; H01J 49/04
[52] U.S. Cl. .................... 204/603; 204/452; 250/288
[58] Field of Search .................... 250/288, 288 A; 204/450, 451, 452, 453, 454, 455, 601, 602, 603, 604

[56] References Cited

U.S. PATENT DOCUMENTS

| | | | |
|---|---|---|---|
| 4,885,076 | 12/1989 | Smith et al. | 204/451 |
| 4,994,165 | 2/1991 | Lee et al. | 204/453 |
| 5,170,053 | 12/1992 | Hail et al. | 250/288 |
| 5,212,365 | 5/1993 | Wiederin | 219/121.52 |
| 5,233,156 | 8/1993 | Chan et al. | 219/121.52 |
| 5,245,185 | 9/1993 | Busch et al. | 250/288 |
| 5,272,308 | 12/1993 | Wiederin | 219/121.52 |
| 5,306,412 | 4/1994 | Whitehouse et al. | 204/452 |

OTHER PUBLICATIONS

Zone Electrophoresis in Open–Tubular Glass Capillaries, Jorganson & Lukacs, Anal. Chem., vol. 53, Jan. 1981.
Capillary Electrophoresis Inductively Coupled Plasma Spectrometer for Rapid Elemental Speciation, Olesik, Kinzer, Olesik, Anal. Chem., vol. 67, Jan. 1995.

*Primary Examiner*—Bruce F. Bell
*Assistant Examiner*—John S. Starsiak, Jr.
*Attorney, Agent, or Firm*—James D. Welch

[57] ABSTRACT

A system for interfacing Capillary Zone Electrophoresis (CZE) systems to Inductively Coupled Plasma-Mass Spectrometer (ICP-MS) sample analysis systems is disclosed. The interface system includes a Sample Introduction Electrophoresis Capillary Tube as an integral part of a modified Direct Injection Nebulizer (DIN) system. During use sample components separated by (CZE) are entered to the modified (DIN) via a sample introduction electrophoresis capillary tube present therein, in which modified (DIN) they are mixed with an entered make-up liquid. The make-up liquid is conductive and serves to make electrophoresis effecting electrical contact to the end of the sample introduction electrophoresis capillary tube in the modified (DIN). The resulting mixture of make-up liquid and separated sample components is nebulized by simultaneous ejection of concentric sample component and make-up liquid mixture and an entered gas flow, to provide a multiplicity of small diameter droplets which are typically injected into an Inductively Coupled Plasma Torch for ionization, prior to entry of resulting ionized sample components to a Mass Spectrometer sample analysis system for detection and analysis thereof. It is noted that the presence of the make-up liquid buffers the effect of the entered nebulizing gas flow upon the capillary zone electrophoresis process, thereby allowing decoupled separate optimization of sample separation and nebulizing processes.

11 Claims, 7 Drawing Sheets

| Metal species | Continuous DIN ICP-MS, pg/mL | CE/ICP-MS, pg/mL |
|---|---|---|
| $Li^+$ | 3 | 50 |
| $K^+$ | 100 | 1000 |
| $Cd^{2+}$ | 6 | 60 |
| $Co^{2+}$ | 1 | 420 |
| $Mn^{2+}$ | 3 | 30 |
| $Pb^{2+}$ | 0.9 | 600 |
| $Sr2$ | 0.3 | 180 |
| $Tl^+$ | 0.4 | 7 |
| As (III) | 20 | 100 |
| As (V) | 20 | 20 |
| Se (IV) | 20 | 300 |
| Se (VI) | 80 | 100 |

The detection limits for DIN ICP-MS were calculated based on the peak-to-peak noise of the CIP-MS blank signal and the detection limits for CE/ICP-MS were calculated based peak-to-peak noise of the CE/ICP-MS electropherogram baseline.

FIG. 12

SYSTEM FOR INTERFACING CAPILLARY ZONE ELECTROPHORESIS AND INDUCTIVELY COUPLED PLASMA-MASS SPECTROMETER SAMPLE ANALYSIS SYSTEMS, AND METHOD OF USE

TECHNICAL FIELD

The present invention relates to interfacing systems and methods for use in chemical analysis systems. More particularly the system of the present invention is a system for interfacing Capillary Zone Electrophoresis systems to Inductively Coupled Plasma-Mass Spectrometer Sample Analysis Systems utilizing a modified Direct Injection Nebulizer system which comprises a sample introduction electrophoresis capillary tube.

BACKGROUND

The solvated sample component separation capability of Capillary Zone Electrophoresis, (CZE), systems is well known. As well, the ability of Direct Injection Nebulizer, (DIN), systems to nebulize small volume samples into a multiplicity of small diameter droplets for entry into, for instance, a closely situated Inductively Coupled Plasma system to ionize said sample components, is well known. Further, the sample analysis capabilities of Inductively Couple Plasma-Mass Spectrometer (ICP-MS), systems are well established. What has to date not been known, however, is a system for interfacing (CZE) systems with (ICP-MS) systems, utilizing a modified (DIN) system which comprises a sample introduction electrophoresis capillary tube. It should be apparent that such a system for interfacing would provide valuable utility.

Briefly, a (CZE) system comprises a capillary tube, one end of which is placed in a source of sample component containing solution, and another end of which is positioned distally. In use a voltage is applied between the ends of said capillary tube such that sample component containing solution is caused to migrate therethrough. Depending on the mass and charge of a sample component therein, and such factors as the PH of the solution forming solvent, different sample components travel through said capillary tube at different velocities, thereby arriving at the distal end thereof in a separated manner.

An (ICP-MS) system comprises an Inductively Coupled Plasma system followed by a Mass Spectrometer. An (ICP) system typically comprises an (ICP) "Torch" with an enclosed space therein in which a plasma is inductively formed by application of high frequency electrical energy, via a coil situated around said enclosed space. An (ICP) Torch, it is mentioned, comprises a "Sample Injector Tube" present concentrically and centrally within various other concentrically surrounding tubes, which various other concentrically surrounding tubes typically project beyond the projecting end of said sample injector tube, thereby providing an enclosed space therewithin, beyond the projecting end of said sample injector tube. Typically, during use, a sample solution is distally nebulized, (ie. atomized into small diameter droplets), and the nebulized droplets are caused to flow through said sample delivery tube into said plasma containing enclosed space. Gas is simultaneously caused to flow through annular spaces between concentric tubes within said (ICP) Torch with the effect being that nebulized sample is directed into the plasma containing enclosed space in a plume. When a sample component is injected into said plasma containing enclosed space of an (ICP) Torch, electrons therein are excited into high energy atomic orbitals and some are even dislodged therefrom, thereby providing ionized sample components. A (MS) system comprises means for identifying ionized, charged, sample components based upon their mass and charge by detecting said ionized charged sample component trajectory in the presence of electric and magnetic fields.

A (DIN) is a system for nebulizing small volumes of sample component containing solution. DIN's comprise a sample delivery tube concentrically centrally present within an essentially elongated tubular space through a "primary body element", such that during use sample component containing solution can be caused to eject from an end of said sample delivery tube simultaneous with the ejecting of a concentric gas from an annular space formed between the outer surface of said sample delivery tube, and the inner surface of the elongated tubular space through said primary body element. Interaction between said ejecting sample component containing solution and said gas causes said sample component containing solution to become nebulized into small droplets.

A Search of relevant references has identified an article titled "Zone Electrophoresis in Open-Tubular Glass Capillaries", by Jorgenson and Lukacs, Anal. Chem. 1981, Vol. 53, 1298–1302. This article describes a system for performing (CZE) in open-tubular glass capillaries with seventy-five (75) micron inner diameter with voltages up to thirty kilovolts (30 KV) applied thereacross to allow electroosmotic flow of positive and negative ions of a variety of sizes such that analysis thereof can occur in a single run.

A Patent to Fassel et al., No. 4,575,609 describes a micro nebulizer which inserts in, and mounts directly to a sample injector tube of a standard (ICP) torch. U.S. Pat. Nos. 5,212,365 and 5,272,308 to Wiederin describe improved (DIN) systems which do not require the presence of an (ICP) Torch sample injector tube as a part of their construction, but rather provide an elongated primary body element with a longitudinally oriented hole therethrough, through which longitudinally oriented hole a centrally located sample delivery tube extends. The Wiederin (DIN) systems allows for easy access to the space inside the Primary Body Element to allow nondestructive cleaning, and allows easy adjustment of the location of the relative positions of the sample ejecting end of the Sample Delivery Tube and the end of the Primary Body Element. Said adjustment allows optimizing the nebulizing ability of the Wiederin (DIN). A Meyer, U.S. Pat. No. 4,990,740 describes a low operational pressure (DIN)-like system at a lower aspect thereof, with a series of impactors thereabove. Said impactors serve to deflect large diameter droplets, (over approximately fifteen (15) microns in diameter), away from injection into an upper aspect of said system.

A Chan et al. U.S. Pat. No. 5,233,156 teaches Torches of the type used in (ICP) systems, which Torches are designed for use with high solids content samples. Standard (ICP) torches are also described therein.

A Smith et al., U.S. Pat. No. 4,885,076 describes a system in which a sample solution is subjected to an electrophoresis process to separate sample components, and in which an electrospray process serves to simultaneously nebulize and ionize the resulting sample solution. Use of a sheath liquid to make electrical contact to a sample solution discharge is mentioned. Another Patent in the same general area is U.S. Pat. No. 4,994,165 to Lee et al. This Patent focuses on a system for providing "make-up" fluid in a "liquid junction system", generally functionally similar to the Smith et al.

system, which make-up fluid replaces fluid lost during the electrospray process. A Patent to Hall et al. describes an electrospray system in which a concentric flow of gas serves to focus the nebulized ionized droplets of an electrospray process.

A very recent article, by Olesik, Kinzer and Olesik titled "Capillary Electrophoresis Inductively Coupled Plasma Sepctrometry for Rapid Elemental Speciation", Anal. Chem. Vol. 67, No. 1, January 1995, describes a combined Capillary zone electrophoresis and pneumatic nebulizer system for use in providing an aerosol for introduction into inductively coupled plasma and mass spectrometer sample analysis systems. The described system provides that a capillary tube be connected within a pneumatic nebulizer system by way of silver paint, said silver paint serving to provide a snug fit thereof within said pneumatic nebulizer, and to provide an electrical contact to the end of the capillary tube thereby allowing electrophoresis effecting voltage to be applied thereto. While the system described is sufficient for investigative purposes, use in a commercial setting would be difficult. In addition, untoward contamination of sample analyte containing capillary effluent with silver, from the silver paint present at the end of the capillary tube can occur.

A need exists for a convenient to use system which provides means for a sample component containing solution to be subjected to a (CZE) process to provide separated sample components, followed by nebulization by a modified (DIN) system comprising a sample introduction electrophoresis capillary tube. Said system, during use, providing a multiplicity of nebulized small diameter sample component containing droplets, followed by injection into a (ICP) system wherein ionization of sample components occurs, which typically is followed by entry to a (MS) system for detection and analysis of the sample component content therein.

The present invention provides the missing teachings.

DISCLOSURE OF THE INVENTION

To understand the present invention it is first necessary to understand the basic functional aspects of Direct Injection Nebulizers, (DIN's), such as that taught in U.S. Pat. No. 5,212,365, to Wiederin. Said (DIN) comprises an elongated Primary Body element with a centrally located longitudinally oriented hole extending therethrough. A Sample Introduction tube extends through said centrally located longitudinally oriented hole. Located on said Primary Body Element is a means for entering a flow of gas which provides access to the annular space formed between the outer surface of said sample introduction tube and the inner surface of the centrally located longitudinally oriented hole through said primary body element. During use a sample component containing solution is caused to flow through said sample introduction tube simultaneous with entry of a flow of gas to said means for entering a flow of gas. Said sample solution and said gas flow simultaneously concentrically exit from one end of said (DIN) elongated primary body element and interact thereat so as to nebulize said sample component containing solution into a multiplicity of small diameter droplets. DIN's are typically situated in an Inductively Couple Plasma (ICP) system such that nebulized sample ejected therefrom is injected directly into said (ICP) system.

The present invention system is a primarily a Direct Injection Nebulizer (DIN) similar to that taught in U.S. Pat. No. 5,212,365 to Wiederin, to which modifications have been made to incorporate a Capillary Zone Electrophoresis (CZE) sample introduction electrophoresis capillary tube therein. In addition, provision is made for entry of "make-up" liquid thereto during use, which make-up liquid serves to provide electrical contact to an end of said sample introduction electrophoresis capillary tube positioned inside said modified (DIN), from which, during use, sample components are caused to exit under the influence of a voltage applied across said sample introduction electrophoresis capillary tube. During use, a distal end of said sample introduction electrophoresis capillary tube is placed into a source of sample component containing solution and, as mentioned, a potential is applied between said source of sample component containing solution and said make-up liquid. Said potential causes sample component containing sample solution to migrate through said sample introduction electrophoresis capillary tube with various sample components present therein migrating at various velocities which are determined by sample component mass, charge, solution PH etc. just as in any (CZE) system. As said sample components exit the sample introduction electrphoresis capillary tube inside said modified (DIN), they are caused to mix with said make-up liquid. Said mixed sample components and make-up liquid then ejects at one end of said modified (DIN) under the influence of make-up liquid flow effecting input pressure, simultaneous with a concentric gas flow entered to said (DIN) at a means for entry thereof on the Primary Body Element thereof, similar to how a sample solution exits a sample delivery tube of a nonmodified (DIN) simultaneous with a concentric gas flow entered thereto.

The sample introduction electrophoresis capillary tube of the modified (DIN) can be thought of as present concentrically within the sample introduction tube of the Wiederin (DIN), with the make-up fluid entered to the annular space between the outer surface of said sample introduction electrophoresis capillary tube and the inner surface of said sample delivery tube, and with said gas flow being in the annular space between the outer surface of the sample delivery tube and the inner surface of the centrally located longitudinally oriented hole through said primary body element.

Said make-up liquid serves not only to provide electrical contact to the end of said sample introduction electrphoresis capillary tube but-also provides a flow of liquid in which sample components exiting from said sample introduction electrophoresis capillary tube can be carried through said (DIN) and ejected therefrom, simultaneously with a gas flow, to provide nebulized sample solution droplets.

It is also noted that the presence of said make-up liquid at the end of the sample introduction electrophoresis capillary tube buffers the effect of said gas flow on sample component migration through said sample introduction electrophoresis capillary tube during use. This is considered an important operational aspect of the present invention as it allows separate, decoupled, optimization of both electrophoresis and nebulization processes.

In the broader sense the present invention can be thought of as a system for interfacing a source of sample component containing solution with an Inductively Coupled Plasma-Mass Spectrometer (ICP-MS) sample analysis system. In use the present invention serves to provide sample components present in a sample solution, in an electrophoresis effected separated sequential manner, to an (ICP) which serves to ionize the resulting nebulized sample components prior to entry thereof to a Mass Spectrometer (MS) for detection and analysis.

It is noted that suitable uncoated fused silica electrophoresis capillary tubes, with inner diameters of fifty (50) to one-hundred-twenty-five (125) micrometers, and with outer diameters of between one-hundred (100) to one-hundred-seventy-five (175) micrometers, for application in the present invention, are available from Polymicro Technologies Inc. in Phoenix Ariz. Also, experimental results presented in the Detailed Description Section of this Disclosure were obtained using an ISCO Model 3850 electrophoresis system available from ISCO Inc. in Lincoln, Nebr., and a Hewlett-Packard Model 4500 ICP-MS system available from Hewlett-Packard in Wilmington, Del.

The present invention can include means for conveniently adjusting the location of the end of the electrophoresis capilliary tube in the sample delivery tube during use without requiring major disassembly. For example, a means for gripping said electrophoresis capillary tube can be provided in a connection means which attaches to modified direct injection nebulizer primary body element by way of screw threads. Rotation of said connection means with respect to said primary body element, it will be appreciated, can then cause translated linear motion of the end of said electrophoresis tube with respect to said sample delivery tube. Said adjustment capability serves to allow optimization of the buffering effect of the presence of said make-up liquid at the end of said electrophoresis capilliary tube, so that separate optimization of the decoupled electrophoresis and nebulization effects can be effected. Likewise, similar means for adjusting the location of the end of the sample delivery tube within the primary body element, to optimize the nebulization process can be present.

It is noted that the present invention can be utilized in conjunction with a spray chamber such that nebulized sample solution is injected thereinto, as well as in systems wherein nebulized sample solution is injected directly into an ICP torch contained plasma.

The present invention will be better understood by reference to the Detailed Description Section of this Disclosure in conjunction with the accompanying Drawings.

SUMMARY OF THE INVENTION

Capillary Zone Electrophoresis, (CZE), is a well known technique for separating sample components present in a sample solution. As well, Direct Injection Nebulization is a well known approach to nebulizing a sample solution into a multiplicity of small diameter droplets. Typically, Direct Injection Nebulizer, (DIN), systems eject nebulized sample solution droplets produced by use thereof, into a closely situated Inductively Coupled Plasma (ICP) system, wherein they are ionized prior to their being caused to enter a Mass Spectrometer, (MS), for detection and analysis therein.

No known reference, however, teaches that (CZE) should be interfaced by a modified (DIN) system to an (ICP-MS) system, or a modified (DIN) system for accomplishing such.

The present invention teaches that (CZE) should be interfaced to an (ICP-MS) system with a modified (DIN), said modification comprising the inclusion of a sample introduction electrophoresis capillary tube in a standard (DIN).

Therefore it is a purpose of the present invention to teach a method for interfacing (CZE) and a (ICP-MS) sample analysis system.

It is a purpose of the present invention to teach that (CZE) and an (ICP-MS) system should be interfaced utilizing a modified (DIN).

It is yet another purpose of the present invention to teach a modified (DIN) system wherein the modification comprises the inclusion of a sample introduction electrophoresis capillary tube in a standard (DIN).

BRIEF DESCRIPTION OF THE DRAWINGS

FIG. 6c shows the system of FIG. 4 inserted into the sample injector tube of the torch in FIG. 6a.

DETAILED DESCRIPTION

Figure 1:
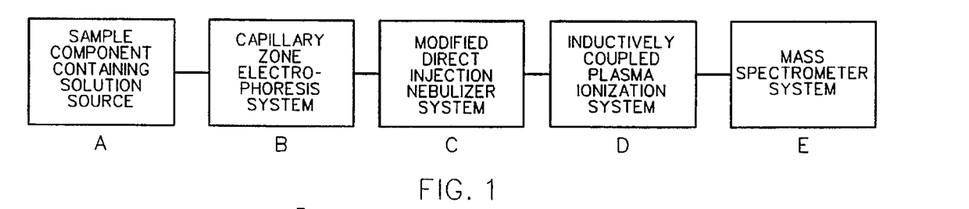
FIG. 1 shows a block diagram of the overall system of the present invention.

Turning now to the Drawings, there is shown in FIG. 1, a block diagram identifying functional components typically required to practice the present invention. Identified are a source of sample component containing solution "A", a Capillary Zone Electrophoresis system "B", a Direct Injection Nebulizer system "C", an Inductively Coupled Plasma Ionization system "D" and a Mass Spectrometer sample analysis system "E". In use sample components in solution are caused, by a capillary zone electrophoresis process, to migrate through a Sample Introduction Electrophoresis Capillary Tube, enter a Direct Injection Nebulizer system and emerge therefrom as a multiplicity of nebulized small diameter droplets which are caused to enter an Inductively Coupled Plasma Ionization system wherein they become ionized, which ionized sample components are then caused to proceed into a Mass Spectrometer wherein they are detected and analyzed.

The system of the present invention is an interface comprising a Modified Direct Injection Nebulizer, in which the modification comprises the addition of a (CZE) system sample introduction electrophoresis capillary tube. That is, the present invention integrates systems "B" and "C" in FIG. 1.

Figures 2, 2P:
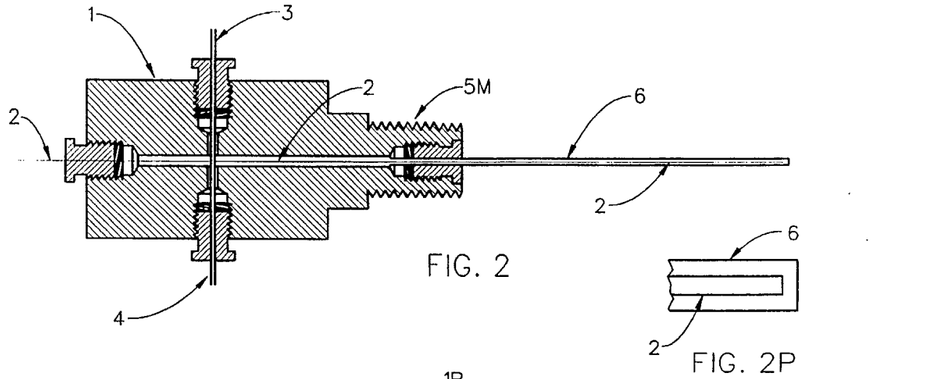
FIG. 2 shows a cross sectional view of a first primary body element of the present invention.
FIG. 2P shows an expanded view of a sample introduction electrophoresis capillary tube inside a sample delivery tube which extends from the present invention first primary body element.
Figures 3, 4, 4P, 5:
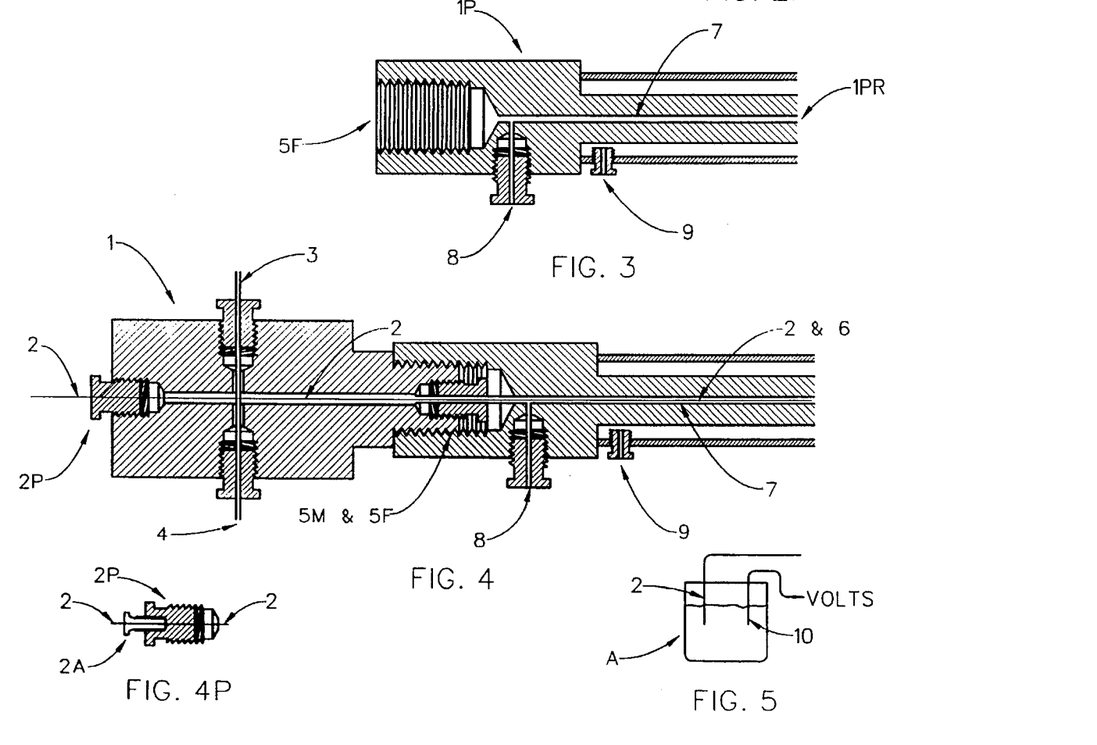
FIG. 3 shows a cross sectional view of a second primary body element of the present invention.
FIG. 4 shows a cross sectional view of first and second primary body elements combined into a system.
FIG. 4P shows a means by which the end of the location of the end of the electrophoresis capillary tube in the sample delivery tube can be conveniently adjusted.
FIG. 5 shows an end of the sample introduction electrophoresis capillary tube distal from the first and second body elements placed into a source of sample component containing solution.

FIGS. 2, 3 and 4 show a preferred embodiment of a present invention integrated combination of a sample introduction electrophoresis capillary tube and modified direct injection nebulizer interface system, enabling practice of the sample solution component separation, nebulization, and detection and analysis procedure recited above. FIG. 2 shows a first primary body element (1) with a sample introduction electrophoresis capillary tube (2) concentrically centrally located within a sample delivery tube (6) which extends from said first primary body element (1). Also shown are a "make-up" liquid entry means (3), electrode (4) and male threads (5M). FIG. 2P makes clear that sample introduction electrophoresis capillary tube (2) is concentrically centrally located inside said sample delivery tube (6), with the end of said sample introduction electrophoresis capillary tube (2) shown at the right side of said FIG. 2P ending within, short of the end of the sample delivery tube (6). Note that an annular space between the outer surface of sample introduction electrophoresis capillary tube (2) and the inner surface of sample delivery tube (6) exists, into which, via make-up liquid entry means (3), make-up liquid can be entered during use. Note that entered make-up liquid can contact the end of sample introduction electrophoresis capillary tube (2) while inside sample delivery tube (6), emphasis added.

FIG. 3 shows a second primary body element (1P) with a centrally located longitudinally oriented hole (7) therethrough, a nebulizer gas entry means (8), a carrier gas entry means (9), and female screw threads (5F) present for interconnecting with first primary body element via male screw threads (5M). FIG. 4 shows the elements of the modified direct injection nebulizer shown in FIGS. 1 and 2, having been assembled into combined Capillary Zone Electrophoresis and Modified Direct Injection Nebulizer system (ie. combined FIG. 1 systems (B) and (C)), by screwing male screw threads (5M) into female screw threads (5F). (Note, rotation of interconnecting male (5M) and femal (5F) screw threads serves to adjust the location of the end of sample delivery tube (6) in second primary body element (1P) and allow optimization of the nebulization effect described supra.) It should then be appreciated that a capillary zone electrophoresis system (B) is an integral component of a modified direct injection nebulizer system (C) in the present invention (CZE)-(ICP-MS) interface system. It is also to be appreciated that the present invention can be constructed as a one element system in which male (5M) and female (5F) screw threads are merged into a continuous material.

As indicated by FIG. 5, during use an end of the sample introduction electrophoresis capillary tube (2) positioned at the left in FIGS. 2 through 4 is placed into a source of sample component containing solution (A). An electrode (10) is also placed thereinto and provided a positive electrical potential, with respect to electrode (4) shown in FIGS. 1 and 4, present in primary body element (1). Said electrode (4) makes electrical contact with "make-up" liquid entered to the annular space between the outer surface of sample introduction electrophoresis capillary tube (2) and the inner surface of sample delivery tube (6), and said make-up liquid contacts the end of said sample introduction electrophoresis capillary tube (2) while inside said sample delivery tube (6) during use. If said make-up fluid is electrically conductive the process of capillary electrophoresis occurs such that sample components, from sample component solution (A) source, migrate, at varying rates, to the end of said sample introduction electrophoresis capillary tube (2) and exit into, and mix with, said make-up liquid. Said make-up liquid is caused to flow by constant entry thereof into make-up liquid entry means (3) on first primary body element. In addition a flow of nebulizer gas is simultaneously entered to nebulizer gas entry means (8) and interaction between said mixture of sample components and make-up liquid and said flow of nebulizer gas simultaneously ejecting from the end of said sample delivery tube (6), shown at the right in FIGS. 2 and 4, causes said mixture of sample components and make-up liquid to be nebulized into a multiplicity of small diameter droplets as it is ejected from the end of sample delivery tube (6). A carrier gas flow can also be entered to carrier gas entry means (9) on second primary body element (1P) shown in FIGS. 3 and 4, to aid with the transport of said multiplicity of nebulized small diameter droplets into an inductively coupled plasma torch, (see FIGS. 6A and 6B) into which the present invention modified (DIN) interface system is inserted during use. It is noted that the presence of make-up liquid at the end of sample introduction electrophoresis capillary tube (2) within sample delivery tube (6) buffers the influence of nebulizer and carrier gas flows and prevents adverse effects on the electrophoresis process inside said sample introduction electrophoresis capillary tube (2). This allows decoupled separate optimization of the (CZE) sample component separation process and the (DIN) nebulization procedure. This is considered an important operational aspect of the present invention. Also note in FIG. 4P that the coupler (2P) can comprise elements 2A and 2P. Element (2A) serves to grip electrophoresis capillary tube (2), such that when element (2P) is rotated in the screw threads in first primary body element (1), the location of the end of electrophoresis capillary tube (2) in sample delivery tube (6) is conveniently adjusted.

Figure 6A:
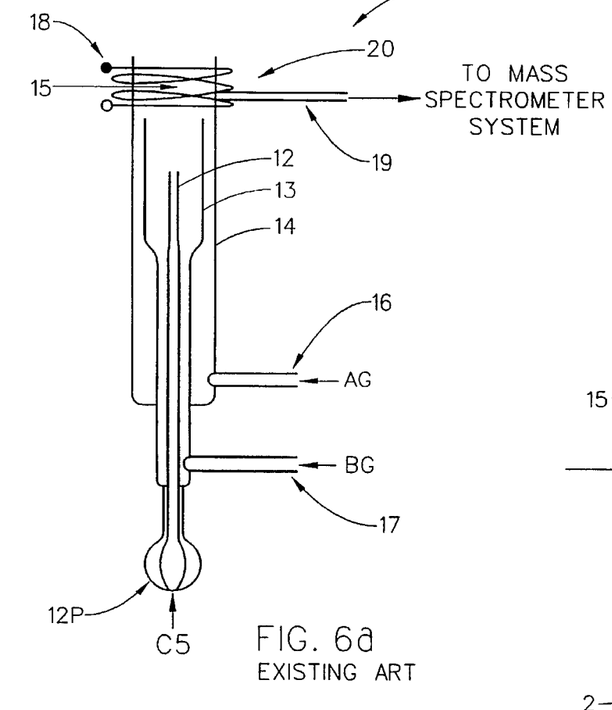
FIG. 6A shows an elevational view of an inductively coupled plasma torch with an R-F coil placed around the upper end thereof.
Figure 6B:
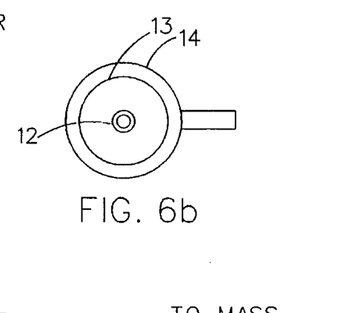
FIG. 6B shows a top view of the inductively coupled plasma torch application of the present invention showing decreased Cs+signal when electrophoresis voltage is turned off.

FIGS. 6A and 6B show a standard inductively couple plasma torch (20) which is a major component of an inductively coupled plasma ionization system, identified as (D) in FIG. 1. Shown are outer tube (14), intermediate tube (13), sample injector tube (12) gas entry ports (16) and (17), and sample entry port (12P). A space (15) within outer tube (14) is shown above said sample injector tube (12). In general use a nebulized sample (CS) is entered at sample entry port (12P) and gas flows (AG) and (BG) are entered at ports (16) and (17), said gas flows (AG) and (BG) serving to guide entered nebulized sample (CS) into space (15) therein wherein a plasma is caused to exist. Note that a coil (18) present around space (15) serves to induce a plasma therein when radio frequency electrical excitation is applied thereto.

Figure 6C:
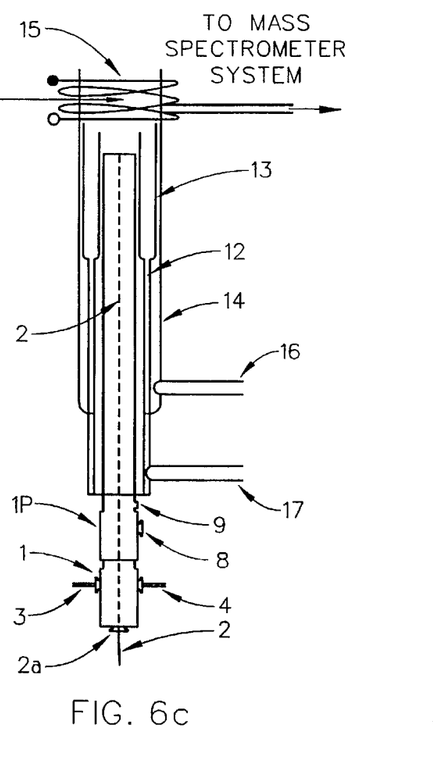

FIG. 6c shows the system of FIG. 4 inserted into the sample injector tube (12) of the inductively coupled plasma torch (20) in FIG. 6a.

In use the right side of primary body element (1PR), shown in FIGS. 3 and 4, inserts into sample entry port (12P) of inductively coupled plasma torch (20), such that a multiplicity of nebulized small diameter droplets ejected therefrom are caused to enter space (15) therein wherein sample components present are ionized by a plasma effected thereat. Said ionized sample components are then caused to enter a mass spectrometer system (E) sample analysis system, via ionized sample interface means (19), for analysis therein.

It is noted that make-up liquid can be similar solvent to that in which the sample components are disolved, or of a different composition. A typical make-up fluid might be an electrically conductive two (2%) percent solution of nitric acid.

It is also mentioned that the sample introduction electrophoresis capillary tube (2) is typically, though not necessarily made of fused silica with inner and outer diameters of fifty (50) and one-hundred (100) micrometers respectively. The sample introduction tube (6) of the present invention is typically, though not necessarily made of polyimide with a one-hundred-eighty (180) micrometer outer diameter and with an inner diameter greater that the outer diameter of the electrophoresis capillary tube, said inner diameter typically being sixty (60) to one-hundred-ten (110) micrometers. A typical length of the primary body element (1P) is one-hundred (100) milimeters with the inner diameter of the centrally located longitudinally oriented hole therethrough being on the order of two-hundred (200) micrometers. It will then be appreciated that a typical annular space radial difference, in which annular space make-up liquid can flow, between the outer surface of the sample introduction electrophoresis capillary tube (2) and the inner surface of the hole through said sample delivery tube (6), of approximately ten (10) micrometers exists. As well, a typical annular space radial difference, in which annular space a nebulizing gas flow can be effected, between the outer surface of the sample delivery tube (6) and the inner surface of the centrally located longitudinally oriented hole in the primary body element (1P), of approximately twenty (20) micrometers exists.

Figure 7:
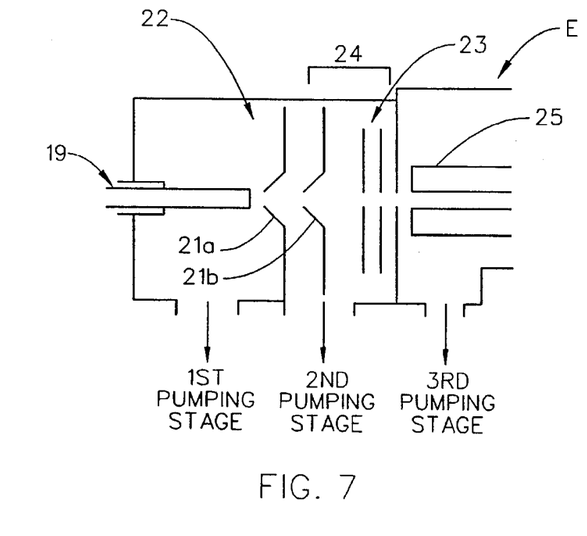
FIG. 7 shows a diagramatic representation of a mass spectrometer system.

FIG. 7 shows the major components of a typical mass spectrometer sample analysis system (E). Shown are ionized sample interface means (19) for entering nebulized ionized sample components to first vacuum chamber (22), skimmer sections (21a) and (21b) through which access is provided to second vacuum chamber (23), ion focusing lens (24), and mass analyzer (25). First, second and third pumping stages are also indicated and serve to provide vacuum levels required. Said first, second and third stage vacuum levels are typically maintained at one, one-times-ten-to-the-minus-forth and five-times-ten-to-the-minus-fifth Torr respectively, with inductively coupled plasma ionization being accomplished at atmospheric pressure in space (15) inside outer tube (14) and above sample injector tube (12) of the Inductively Coupled Plasma Torch of FIGS. 6A and 6B.

It is to be understood that the present invention as demonstrated in FIGS. 1 though 4 can be realized with any functional arrangement in which electrode (4) provides electrical contact to make-up liquid and make-up liquid entry means (3) electrode (4) need not be oriented exactly as shown. In particular, as mentioned infra, the present invention can be of a single primary body element construction in which screw threads (5M) and (5F) are essentially merged in FIG. 4.

EXPERIMENTAL RESULTS

The present invention (CZE) to (ICP-MS), combination (CZE) and modified (DIN) interface, was tested utilizing a standard stock solution containing Li++, K+, Cs++, Cd++, Co++, Mn++, Pb++, Sr++, Ti+and Y+++, at one-thousand (1000) micrograms per mililiter per metal in two (2%) percent nitric acid, available from Inorganic Venture Inc. in Lakewood, N.J. or Fisher Scientific Inc. in Fair Lawn, N.J. A multistock solution containing said elements at a two (2) nanogram-per-militer level was prepared from said stock by dilution.

A (CZE) flow of less than one (1) microliter-per-minute through a twenty-five (25) centimeter long sample introduction electrophoresis capillary tube (2), (see FIGS. 2 and 4), effected by application of thirty-thousand (30,000 KV) kilovolts thereacross, a make-up liquid flow rate of fifteen (15) microliters per minute entered to make-up liquid entry means (3), and a carrier gas flow rate of three-tenths (0.3) liter-per-minute, entered to carrier gas entry means (9), were effected in capillary zone electrophoresis and modified direct injection nebulizer system (ie. systems (B) and (C) in FIG. 1). Nebulizing gas was entered to nebulizing gas entry means (8) at seventy (70) pounds-per-square-inch (psi) and flow rate of six-tenths (0.6) liter-per-minute. Said capillary zone electrophoresis and modified direct injection nebulizer combined system was inserted into the sample injector tube of a CETAC H-23 (ICP) torch, similar to that shown in FIGS. 6A and 6B, (available from CETAC Inc. in Omaha, Nebr.), with the sample ejecting end thereof positioned only a few milimeters from the base of a plasma effected in area (15), (see FIG. 6), therein by application of thirteen-hundred (1300) watts of radio frequency, (ie. megahertz), power to coil (18), while a cooling gas flow (AG), (see FIG. 6A) of fifteen (15) liters-per-minute was entered to port (16) and an auxiliary gas flow (BG) of seven-tenths (0.7) liter-per-minute was entered to port (17). The nebulized sample leaving the capillary zone electrophoresis and modified direct injection nebulizer combined system was at a high velocity of approximately one-hundred-twenty (120) meters-per-second. It is emphasized that all sample components eluting from the electrophoresis capillary tube (2) into the make-up liquid enter the plasma in area (15) of the (ICP) torch shown in FIG.(6A) in a tight plume. Mass spectrometer first, second and third pumping stages, (see FIG. 7) were controlled at one (1) Torr, five (5) times-ten-to-the-minus-forth Torr, and five (5.0) times-ten-to-the-minus-fifty Torr respectively.

It was found that the make-up liquid flow rate was sufficient to prevent any noticeable suction or back-pressure effect on the sample component containing solution in the electrophoresis capillary tube (2).

Figure 8:
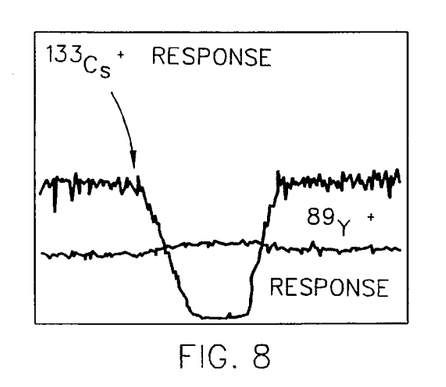
FIG. 8 shows mass-spectrometer experimentally derived results of application of the present invention, showing decreased $Cs^+$signal when electrophoresis voltage is turned off.
Figure 9A:
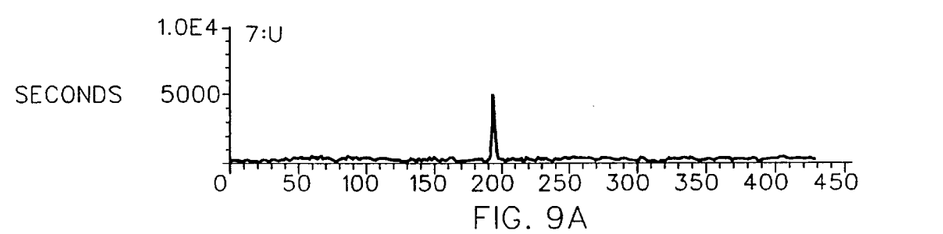
FIGS. 9A through 9J show mass spectrometer experimentally derived peaks for Li, K, Mn, Co, Sr, Y, Cd, Cs, Ti and Pb as functions of time during an application of the present invention.
Figure 9B:
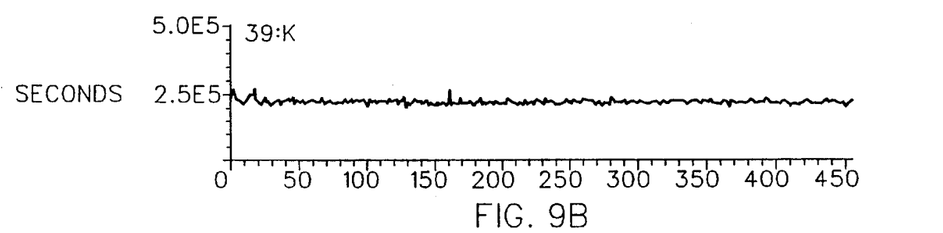
Figure 9C:
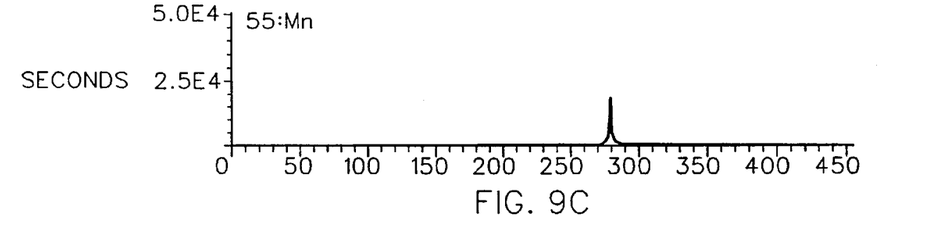
Figure 9D:
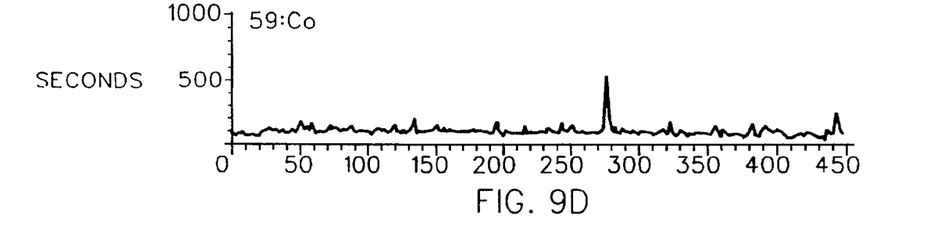
Figure 9E:
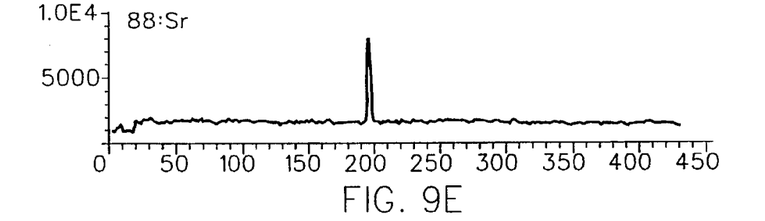
Figure 9F:
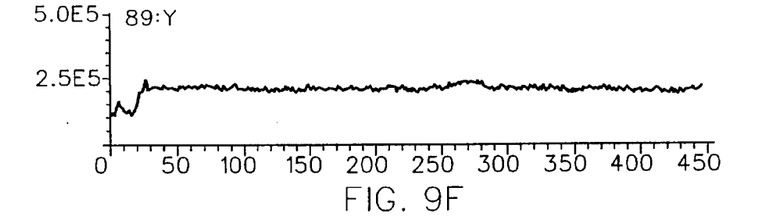
Figure 9G:
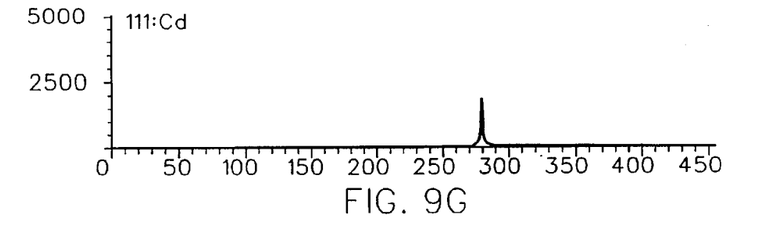
Figure 9H:
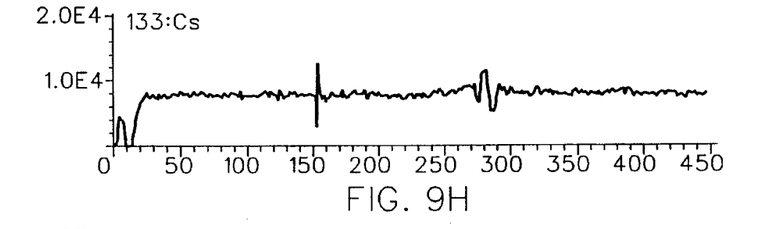
Figure 9I:
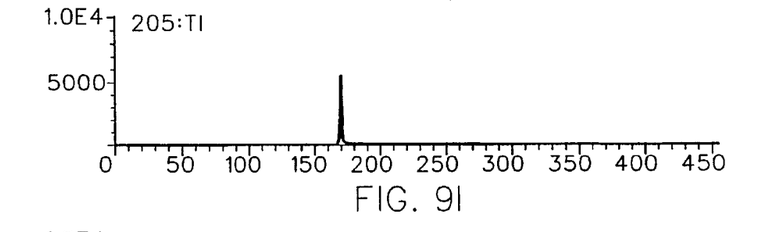
Figure 9J:
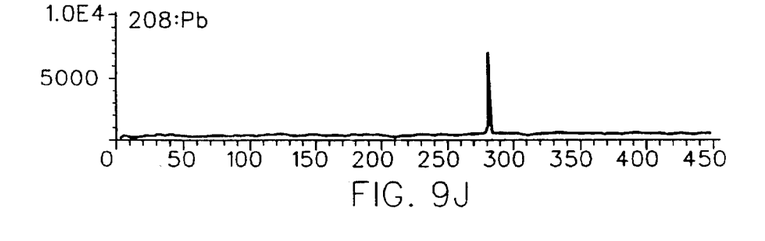

Turning now to FIG. 8, there is shown a typical time plot of 133 Cs+ and 85Y+ in which the valley in the 133 Cs+ plot corresponds to a time during which the electrophoresis voltage was turned off.

FIGS. 9a through 9j show, as a function of time, when various of the sample components identified above, provided by the electrophoresis process as mediated by the present invention modified direct injection nebulizer (C) (CZE)-(ICP-MS) interface system, are detected by the mass spectrometer sample analysis system (E).

In addition, individual stocks of As(III), As(V) monomethylarsonic acid (MMA), dimethylarsinic acid (DMA), Se(IV) and Se(VI) at one-hundred (100) micrograms-per-mililiter as or Se were prepared from NaAsO2, KHAs)4, CH3H2AsO3, (Ch3)2HAsO2, Na2SeO3 and Na2SeO4 respectively. Solutions containing lower concentrations of Se and As species were prepared by compositing individual stock solutions and diluting the composite solution with deionized water as needed.

For (CZE) separation of alkali/alkaline earth and transition metal ions, an electrophoresis buffer solution containing ten (10) mM ammonium nitrate, five (5) nM phenanthroline, and fifty (50) nanograms-per-mililiter was prepared by dissolving appropriate amounts of the chemicals in deionized water and adjusting the solution pH to 8.75 with a 0.1M ammonium hydroxide solution. Another electrophoresis buffer solution used in the (CZE) separation of Se and As species was obtained from Dionex Corporation, (Cat. No. 044138) in Sunnyvale, Calif. This buffer solution consisted of 2.3 nM pyrometalic acid, 6.5 nM sodium hydroxide, 1.6 nM triethanolamine and 0.75 nM hexamethonium hydroxide at a pH of 7.7. Hexamethonium hydroxide was added as a cationic flow modifier. A solution of 50 nanograms-per-liter in two (2) percent nitric acid was prepared and used as needed for the make-up liquid.

Figure 10A:
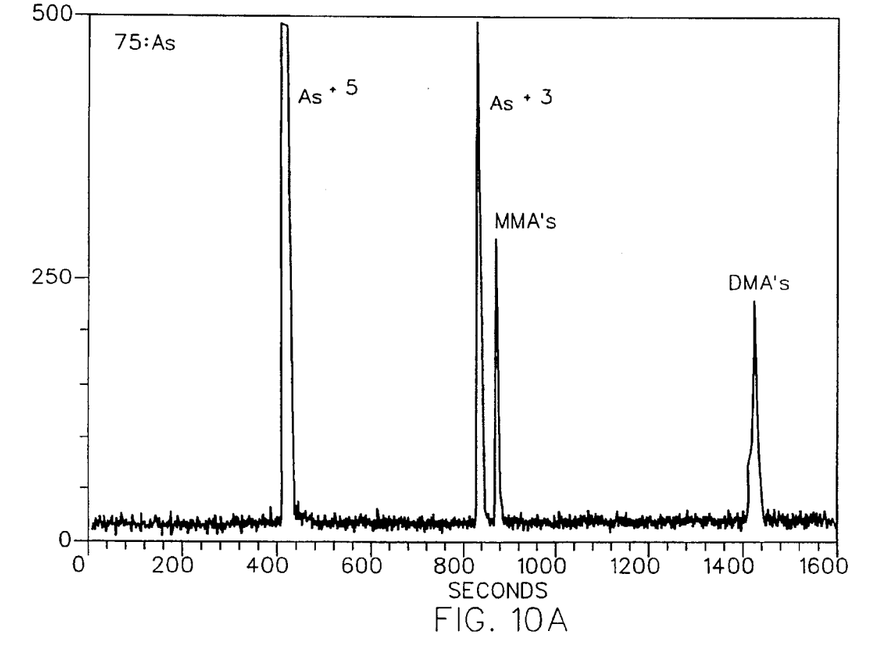
FIG. 10A show mass spectrometer experimentally derived peaks for As in various states of ionization and MMA and DMA peaks as a function of time during an application of the present invention.
Figure 10B:
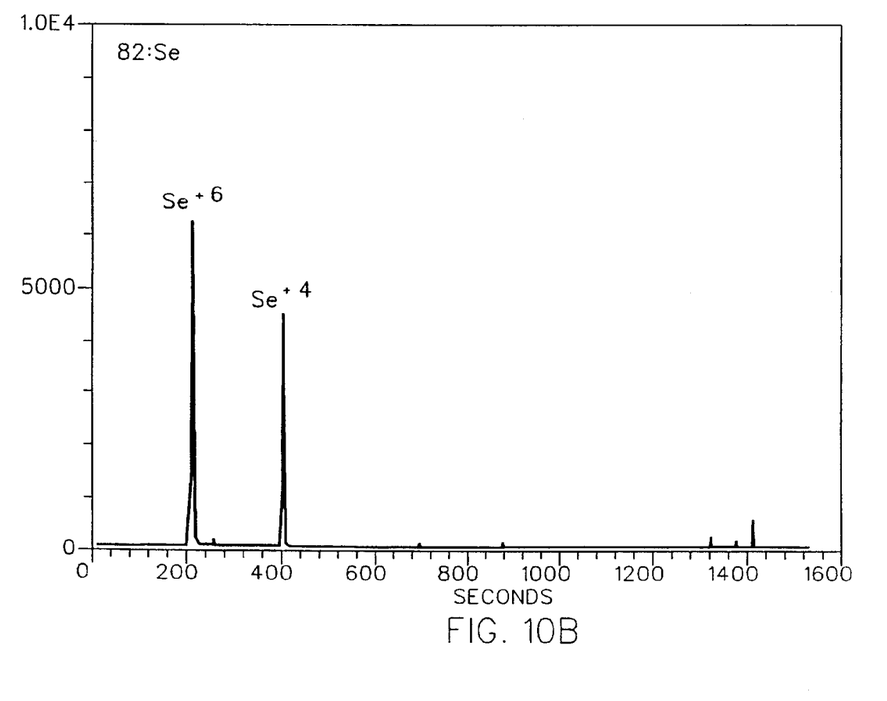
FIG. 10B show mass spectrometer experimentally derived peaks for Se in two ionization states as a function of time during an application of the present invention.

FIGS. 10a and 10b show (CZE)-(ICP-MS) separation results obtained from a sample containing As(III), As(V), MMA and DMA at five-hundred (500) nanograms-per-mililiter.

Figure 11A:
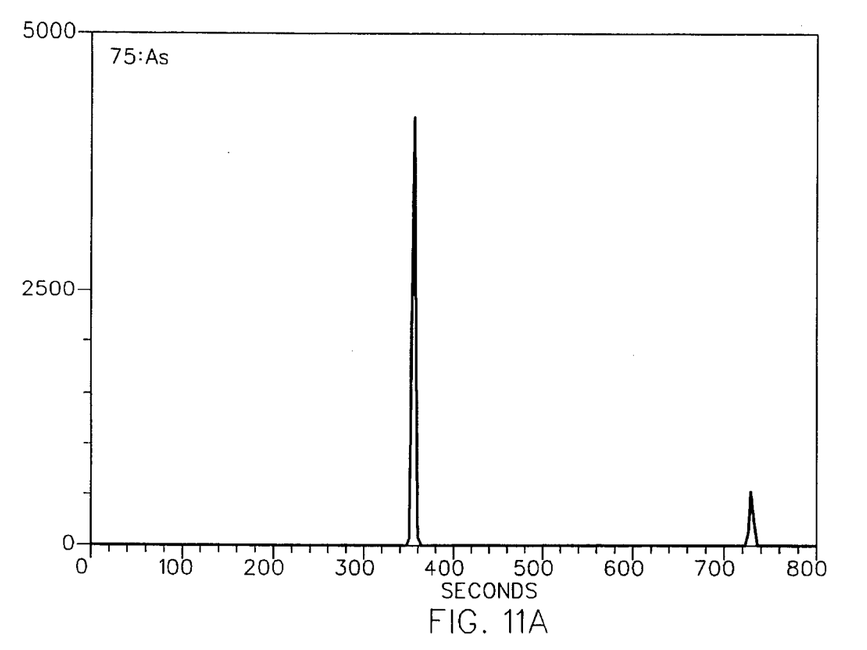
FIG. 11A shows mass spectrometer experimentally derived As peaks as a function of time during an application of the present invention.
Figure 11B:
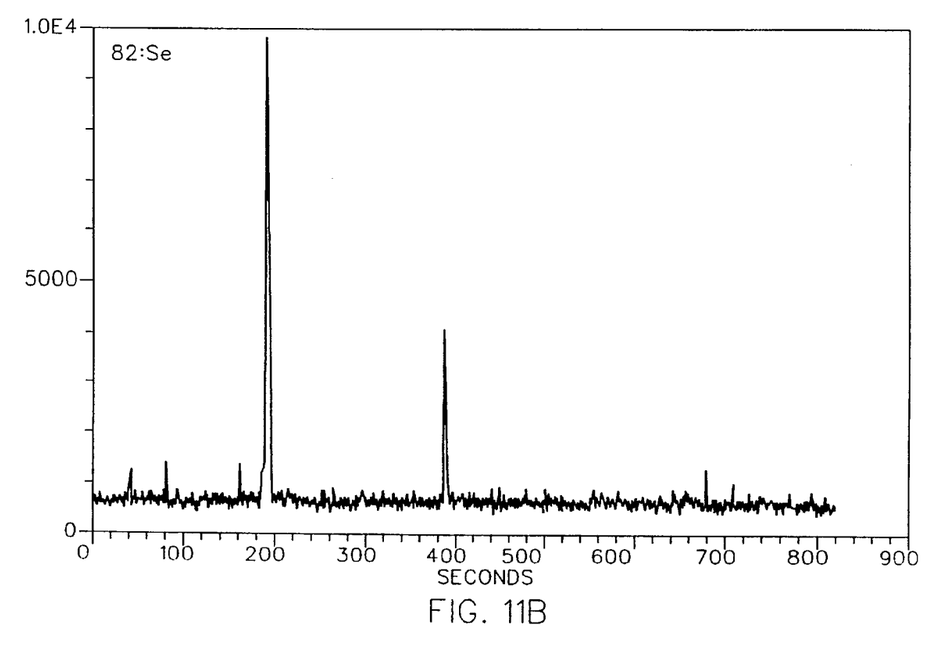
FIG. 11B shows mass spectrometer experimentally derived Se peaks as a function of time during an application of the present invention.

FIGS. 11a and 11b show results (CZE)-(ICP-MS) separation results obtained utilizing a sample containing As(III), As(V), Se(IV) and Se(VI) at two (2) nanograms-per-mililiter.

Note that excellent peak shapes and signal-to-noise ratios are achieved for the As and Se results shown in FIGS. 10a, 10b, 11a and 11b.

Figure 12:
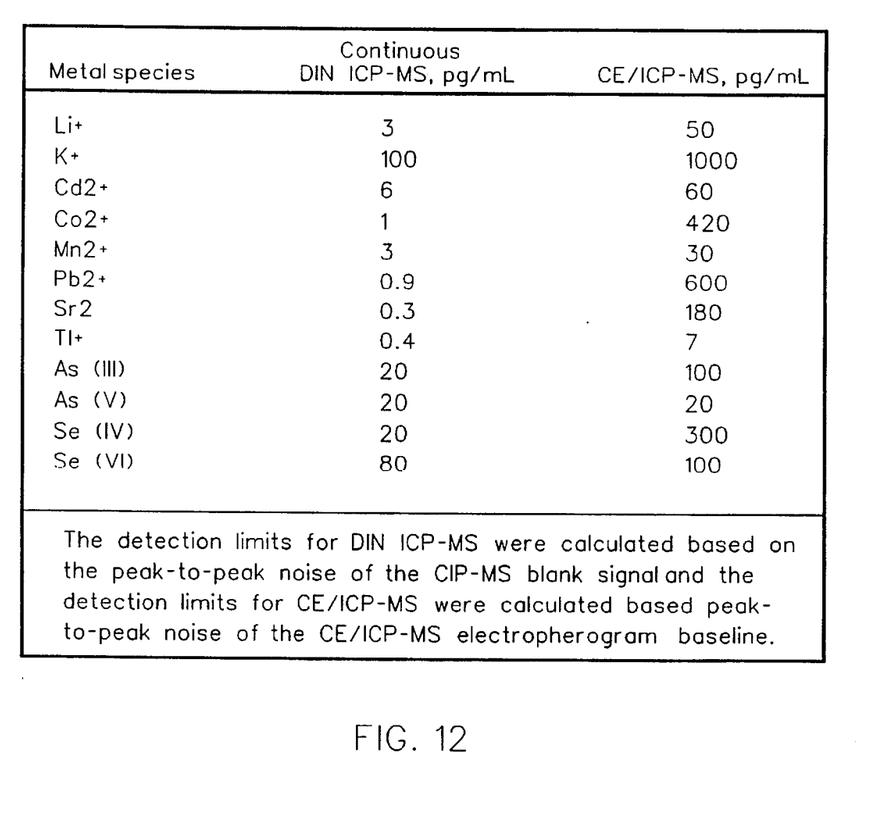
FIG. 12 provides data pertaining to detection limits for Metal species investigated with the present invention as compared to detection limits of direct injection nebulizer application without a capillary zone electrophoresis in place.

FIG. 12 summarizes detection limits obtained from a system utilizing a DIN-ICP-MS system and from the (CZE-Modified DIN combination interface)-(ICP-MS) system of the present invention. For the metal elements investigated the present invention provided detection limits two (2) to six-hundred (600) times better. It is expected that even better results can be achieved using the system of the present invention.

It can be concluded that the (CZE-Modified DIN interface)-(ICP-MS) system described herein and shown in FIGS. 2 through 4, provides a highly effective and efficient means for coupling (CZE) to (ICP-MS) systems.

Also, it is emphasised that as the present invention system is a modified commercially available direct injection nebulizer, (eg. CETAC Technologies MICRONEB-2000), and as the flow of make-up liquid decouples the electrophoresis effect from the nebulization effect, the (DIN) system can be optimized independently of the (CZE) system. The present invention then, can be used with different electrophoresis buffers and applied voltages so that (CZE) conditions can be optimized to achieve rapid separation of analytes. Preliminary results show that the present invention can be utilized to determine target metal species at low parts-per-trillion levels.

Finally, it is to be understood that the present invention can be utilized with a remotely situated spray chamber, in which nebulized sample solution is injected thereinto, as well as in systems wherein nebulized sample is injected directly into an ICP torch contained plasma. As a result, in the primary Claims the term "nebulizer" is utilized, rather than "modified direct injection nebulizer". The purpose is to avoid the possibility of an unnecessarily narrow interpretation of the present invention which would require injection of nebulized sample solution only directly into a plasma in an ICP torch, as is the typical industry understanding when the terms "direct injection nebulizer" are utilized without further explanation. The term "nebulizer" shall be interpreted to mean a "modified direct injection nebulizer" system as described above, but which can be used in other than a "direct injection mode".

Having hereby disclosed the subject matter of this invention, it should be obvious that many modifications, substitutions and variations of the present invention are possible in light of the teachings. It is therefore to be understood that the invention may be practiced other than as specifically described, and should be limited in breadth and scope only by the Claims.

We claim:

1. A system for interfacing capillary zone electrophoresis with inductively coupled plasma-mass spectrometer sample analysis systems comprising a nebulizer, said nebulizer comprising:

a. an elongated primary body element with a centrally located longitudinally oriented hole therethrough;

b. a concentric centrally located sample delivery tube present inside said centrally located longitudinally oriented hole through said primary body element;

c. a concentric centrally located capillary electrophoresis tube present inside said sample delivery tube;

d. means on said primary body element for entering a flow of gas into an annular space between an outer surface of said concentric centrally located sample delivery tube and an inner surface of said longitudinally oriented hole through said primary body element;

e. means for entering a flow of make-up liquid into the annular space between an outer surface of said concentric centrally located sample capillary electrophoresis tube and an inner surface of said concentric centrally located sample delivery tube;

f. means for entering a sample component containing solution to said concentric centrally located capillary tube from a source of sample component containing solution into which it is inserted at an end thereof distal to that present in said primary body element; and g. said system for interfacing capillary zone electrophoresis with inductively coupled plasma-mass spectrometer sample analysis systems further comprising a torch, said torch comprising a centrally located sample injector tube concentrically surrounded by at least an outer tube, said nebulizer being present inside said centrally located sample injector tube, such that a space exists within said outer tube and above said sample injector tube.

2. A system for interfacing capillary zone electrophoresis with inductively coupled plasma-mass spectrometer sample analysis systems comprising a nebulizer, said nebulizer comprising:

a. an elongated primary body element with a centrally located longitudinally oriented hole therethrough;

b. a concentric centrally located sample delivery tube present inside said centrally located longitudinally oriented hole through said primary body element;

c. a concentric centrally located capillary electrophoresis tube present inside said sample delivery tube;

d. means on said primary body element for entering a flow of gas into an annular space between an outer surface of said concentric centrally located sample delivery tube and an inner surface of said longitudinally oriented hole through said primary body element;

e. means for entering a flow of make-up liquid into the annular space between an outer surface of said concentric centrally located sample capillary electrophoresis tube and an inner surface of said concentric centrally located sample delivery tube;

f. means for entering a sample component containing solution to said concentric centrally located capillary tube from a source of sample component containing solution into which it is inserted at an end thereof distal to that present in said primary body element;

said nebulizer of said system for interfacing capillary zone electrophoresis with inductively coupled plasma-mass spectrometer sample analysis systems further comprising at least one additional means selected from the group consisting of:
   a. means for conveniently adjusting the location of the end of said electrophoresis capillary tube within said sample delivery tube; and
   b. means for conveniently adjusting the location of the end of the sample delivery tube with respect to the primary body element.

3. A system for interfacing capillary zone electrophoresis sample component separation capability with inductively coupled plasma-mass spectrometer sample analysis systems comprising a nebulizer system, said nebulizer comprising:
   a. an elongated primary body element with a centrally located longitudinally oriented hole therethrough;
   b. a concentric centrally located sample delivery tube present inside said centrally located longitudinally oriented hole through said primary body element;
   c. a concentric centrally located sample introduction electrophoresis capillary tube present inside said sample delivery tube;
   d. means on said primary body element for entering a flow of gas into an annular space between an outer surface of said concentric centrally located sample delivery tube and an inner surface of said centrally located longitudinally oriented hole through said primary body element;
   e. means for entering a flow of make-up liquid into an annular space between an outer surface of said concentric centrally located sample introduction electrophoresis capillary tube and an inner surface of said concentric centrally located sample delivery tube;
   f. means for entering a sample component containing solution to said concentric centrally located sample introduction electrophoresis capillary tube from a source of sample component containing solution into which it is inserted, at an end thereof distal to that present in said primary body element; and
   g. an inductively coupled plasma system means;
   such that during use an electrical potential is applied between said source of sample component containing solution and the end of said concentric centrally located sample introduction electrophoresis capillary tube inside said primary body element, said end of said concentric centrally located sample introduction electrophoresis capillary tube present in said primary body element being electrically contacted by said make-up fluid flowing in the annular space between the outer surface of said concentric centrally located sample introduction electrophoresis capillary tube and the inner surface of said concentric centrally located sample delivery tube such that sample components are caused to travel through said concentric centrally located sample introduction electrophoresis capillary tube by electrophoresis, said sample components and said make-up liquid becoming mixed as said sample components exit from said concentric centrally located sample introduction electrophoresis capillary tube, such that said sample components, being separated by electrophoresis, are carried along with said make-up liquid;
   such that during use a flow of gas is simultaneously entered to said annular space between the outer surface of said concentric centrally located sample delivery tube and the inner surface of said centrally located longitudinally oriented hole through said primary body element such that said flow of gas and said mixture of make-up liquid and electrophoresis separated sample components eject simultaneously and interact such that a multiplicity of nebulized small diameter sample component containing droplets are formed; and
   such that during use said multiplicity of nebulized small diameter droplets are caused to enter said inductively coupled plasma system means and become ionized when a plasma is induced therein.

4. A system for interfacing capillary zone electrophoresis sample component separation capability with inductively coupled plasma-mass spectrometer sample analysis systems as in claim 3, in which the inductively coupled plasma means comprises a torch, said torch comprising a centrally located sample injector tube concentrically surrounded by at least an outer tube, said nebulizer being present inside said centrally located sample injector tube, such that a space exists within said outer tube and above said sample injector tube into which space the multiplicity of nebulized small diameter sample component containing droplets are caused to enter and become ionized when, during use, a plasma is induced in said space by application of radio frequency voltage to a coil surrounding said space.

5. A system for interfacing capillary zone electrophoresis with inductively coupled plasma-mass spectrometer sample analysis systems comprising a nebulizer as in claim 3 which further comprises means for conveniently adjusting the location of the end of said electrophoresis capillary tube within said sample delivery tube.

6. A system for interfacing capillary zone electrophoresis with inductively coupled plasma-mass spectrometer sample analysis systems comprising a nebulizer as in claim 5 which further comprises means for conveniently adjusting the location of the end of said sample delivery tube with respect to the primary body element.

7. A system for interfacing capillary zone electrophoresis with inductively coupled plasma-mass spectrometer sample analysis systems comprising a nebulizer as in claim 6 in which the primary body element comprises multiple sections and in which the means for conveniently adjusting the location of the end of said sample delivery tube with respect to said primary body element comprise interconnecting screw threads between two sections of said primary body element, such that rotation of one section of said primary body element with respect to said other section causes linearly translated motion of said primary body element with respect to the end of said sample delivery tube.

8. A system for interfacing capillary zone electrophoresis with inductively coupled plasma-mass spectrometer sample analysis systems comprising a nebulizer as in claim 5 in which the means for conveniently adjusting the location of the end of said electrophoresis capillary tube within said sample delivery tube comprise interconnecting screw threads between an electrophoresis capillary tube coupler and said primary body element, such that rotation of said coupler causes linearly translated motion of the end of said electrophoresis tube within said sample delivery tube.

9. A system for interfacing capillary zone electrophoresis sample component separation capability with inductively coupled plasma-mass spectrometer sample analysis systems comprising a nebulizer system, said nebulizer comprising:

a. an elongated primary body element with a centrally located longitudinally oriented hole therethrough;

b. a concentric centrally located sample delivery tube present inside said centrally located longitudinally oriented hole through said primary body element;

c. a concentric centrally located sample introduction electrophoresis capillary tube present inside said sample delivery tube;

d. means on said primary body element for entering a flow of gas into an annular space between the outer surface of said concentric centrally located sample delivery tube and an inner surface of said centrally located longitudinally oriented hole through said primary body element;

e. means for entering a flow of make-up liquid into an annular space between an outer surface of said concentric centrally located sample introduction electrophoresis capillary tube and an inner surface of said concentric centrally located sample delivery tube;

f. means for entering a sample component containing solution to said concentric centrally located sample introduction electrophoresis capillary tube from a source of sample component containing solution into which it is inserted, at an end thereof distal to that present in said primary body element;

such that during use an electrical potential is applied between said source of sample component containing solution and the end of said concentric centrally located sample introduction electrophoresis capillary tube inside said primary body element, said end of said concentric centrally located sample introduction electrophoresis capillary tube present in said primary body element being electrically contacted by said make-up fluid flowing in the annular space between the outer surface of said concentric centrally located sample introduction electrophoresis capillary tube and the inner surface of said concentric centrally located sample delivery tube such that sample components are caused to travel through said concentric centrally located sample introduction electrophoresis capillary tube by electrophoresis, said sample components and said make-up liquid becoming mixed as said sample components exit from said concentric centrally located sample introduction electrophoresis capillary tube, such that said sample components, being separated by electrophoresis, are carried along with said make-up liquid; and such that during use a flow of gas is simultaneously entered to said annular space between the outer surface of said concentric centrally located sample delivery tube and the inner surface of said centrally located longitudinally oriented hole through said primary body element such that said flow of gas and said mixture of make-up liquid and electrophoresis separated sample components eject simultaneously and interact such that a multiplicity of nebulized small diameter sample component containing droplets are formed;

said system for interfacing capillary zone electrophoresis sample component separation capability with inductively coupled plasma-mass spectrometer sample analysis systems further comprising at least one additional means selected from the group consisting of:

a. a means for conveniently adjusting the location of the end of said electrophoresis capillary tube within said sample delivery tube; and b. a means for conveniently adjusting the location of the end of said sample delivery tube with respect to the primary body element.

10. A system for interfacing capillary zone electrophoresis with inductively coupled plasma-mass spectrometer sample analysis systems comprising a nebulizer as in claim 9 in which the means for conveniently adjusting the location of the end of said electrophoresis capillary tube within said sample delivery tube comprise interconnecting screw threads between an electrophoresis capillary tube coupler and said primary body element, such that rotation of said coupler causes linearly translated motion of the end of said electrophoresis tube within said sample delivery tube.

11. A system for interfacing capillary zone electrophoresis with inductively coupled plasma-mass spectrometer sample analysis systems comprising a nebulizer as in claim 9 in which the primary body element comprises multiple sections and in which the means for conveniently adjusting the location of the end of said sample delivery tube with respect to said primary body element comprise interconnecting screw threads between two sections of said primary body element, such that rotation of one section of said primary body element with respect to said other section causes linearly translated motion of said primary body element with respect to the end of said sample delivery tube.

* * * * *

UNITED STATES PATENT AND TRADEMARK OFFICE
Certificate

Patent No. 5,597,467                                                 Patented: January 28, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jianzhong Zhu, Daniel R. Wiederin, Victoria Lopez-Avila and Yan Liu.

Signed and Sealed this Thirty-First Day of October, 2000.

JILL WARDEN
*Supervisory Patent Examiner*
Art Unit 1743

UNITED STATES PATENT AND TRADEMARK OFFICE
Certificate

Patent No. 5,597,467                                    Patented: January 28, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of the patent is: Jianzhong Zhu, Daniel R. Wiederin, Viorica Lopez-Avila and Yan Liu.

Signed and Sealed this Twentieth Day of March, 2001.

JILL WARDEN
*Supervisory Patent Examiner*
Art Unit 1743